US00PP11787P2

(12) United States Plant Patent
Green et al.

(10) Patent No.: US PP11,787 P2
(45) **Date of Patent: *Feb. 27, 2001**

(54) MANDEVILLA PLANT WITH DOUBLE FLOWER CALLED 'RITA MARIE GREEN'

(75) Inventors: James Mitchell Green; Cecil Michael Green, Jr.; Rita Marie Green, all of Haines City, FL (US)

(73) Assignee: Monrovia Nursery Company, Azusa, CA (US)

( * ) Notice: Under 35 U.S.C. 154(b), the term of this patent shall be extended for 0 days.

This patent is subject to a terminal disclaimer.

(21) Appl. No.: 09/137,554

(22) Filed: Aug. 20, 1998

(51) Int. Cl.[7] ..... A01H 5/00
(52) U.S. Cl. ..... Plt./232
(58) Field of Search ..... Plt./232; 800/298, 800/323

(56) References Cited

PUBLICATIONS

Color photograph of MandeVilla plant 'Monite' (1 page).
Letter bearing a date of Aug. 22, 1996 from Mike C. Green (11 pages).
Memo entitled MN–AZUSA dated Sep. 4, 1996 (3 pages).
J. Mitchell Green letter bearing the notation Jun. 21, 1997 (wrote) mailed Jul. 1, 1997 (8 pages).
Letter from Monrovia to Mitchell Green bearing facsimile notation of Aug. 21, '97 (1 page).

*Primary Examiner*—Lynette R. F. Smith
*Assistant Examiner*—Melissa L. Kimball
(74) *Attorney, Agent, or Firm*—Klarquist Sparkman Campbell Leigh & Whinston LLP

(57) ABSTRACT

A new and distinct Mandevilla variety characterized by red to red-purple double flowers having five parted outer corolla and inner five parted ring of petaloids.

3 Drawing Sheets

BACKGROUND OF THE INVENTION

The present invention relates to a new variety of Mandevilla plant, called 'Rita Marie Green'. This plant is believed to be different from all previous known Mandevilla plants in that it possesses double flowers. 'Rita Marie Green' is useful as a woody vine that produces decorative double blossoms. The double flowers of 'Rita Marie Green' enhance its appearance and make it especially marketable, and therefore, useful. The botanical name for my new variety is *Mandevilla×amabilis* 'Rita Marie Green'.

The progenitor plant of 'Rita Marie Green' was a Mandevilla of the variety 'Alice du Pont', which does not have double flowers. 'Alice DuPont' is botanically known as *Mandevilla×amabilis* (an interspecific hybrid of *M. splendens* and an undefined parent), and therefore has the complete botanical name *Mandevilla×amabilis* 'Alice DuPont'.

The parent plant of the new variety was found in a group of 'Alice du Pont' Mandevilla plants growing in a cultivated area (in a greenhouse) in Haines City, Fla. Thus, the new plant is understood to be a mutation of the 'Alice du Pont' variety of Mandevilla plant. The new plant has been propagated from cuttings taken from the parent plant and from progeny produced from such cuttings. My new variety, 'Rita Marie Green,' has been grown from at least five successive generations of cuttings and each generation has only generated plants that express double flowers (i.e. a first cutting has been taken grown to maturity and then used to provide the cutting for the next generation). In addition, culturing of the 'Rita Marie Green' variety auxillary bud tissue has also only produced plants with double flowers. Hence, the double flower phenotype is stable.

'Rita Marie Green' has not been observed under all possible environmental conditions and its phenotype may vary significantly with variations in environment such as temperature, light intensity, and day length, without any variation in genotype. However, the following unique charactristic has been repeatedly observed in asexually propagated progeny of 'Rita Marie Green' and distinguish it from all other Mandevilla varieties: double flowers which are red to red-purple and comprise an outer corolla of five petals or limbs and an inner flower comprising a ring of petaloids. This double flower structure is unique among Mandevilla plants and is a characteristic of all 'Rita Marie Green' variety plants, including the variety 'Monite'. The inner petaloids comprise five inner petaloids in a cluster within the outer corolla limbs. In some cases, the inner petaloids assume an upright or trumpet-like configuration generally prohibiting a view of the inner throat and forming a "flower-within-flower" cluster; in other cases, the inner petaloids are more laid back against the outer petals, exposing the throat of the plant; in relatively rare instances, the inner petaloids assume a folded, almost rose-like appearance or, alternatively, a windmill-like appearance. However, in all cases, the flower within a flower characteristic of this new Mandevilla variety is outstanding.

This double flowering characteristic is established and transmitted through succeeding asexual propagations. There are several double flower forms that have been exhibited by this plant, as described below.

BRIEF DESCRIPTION OF THE PHOTOGRAPHS

The following drawings are photographs of 'Rita Marie Green.'

DETAILED DESCRIPTION

Figure 1:
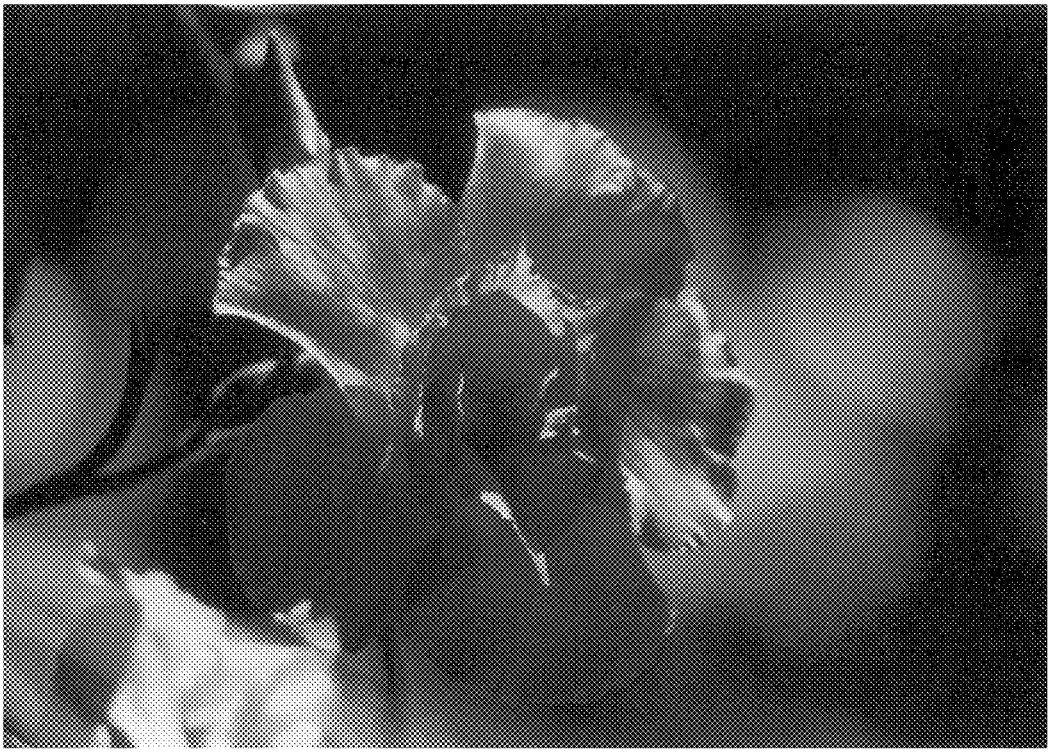
FIG. 1 is an anterior view of the double flower bloom of 'Rita Marie Green' showing the double flower structure made up of outer five-parted corolla limbs and inner five-parted petaloids.
Figure 2:
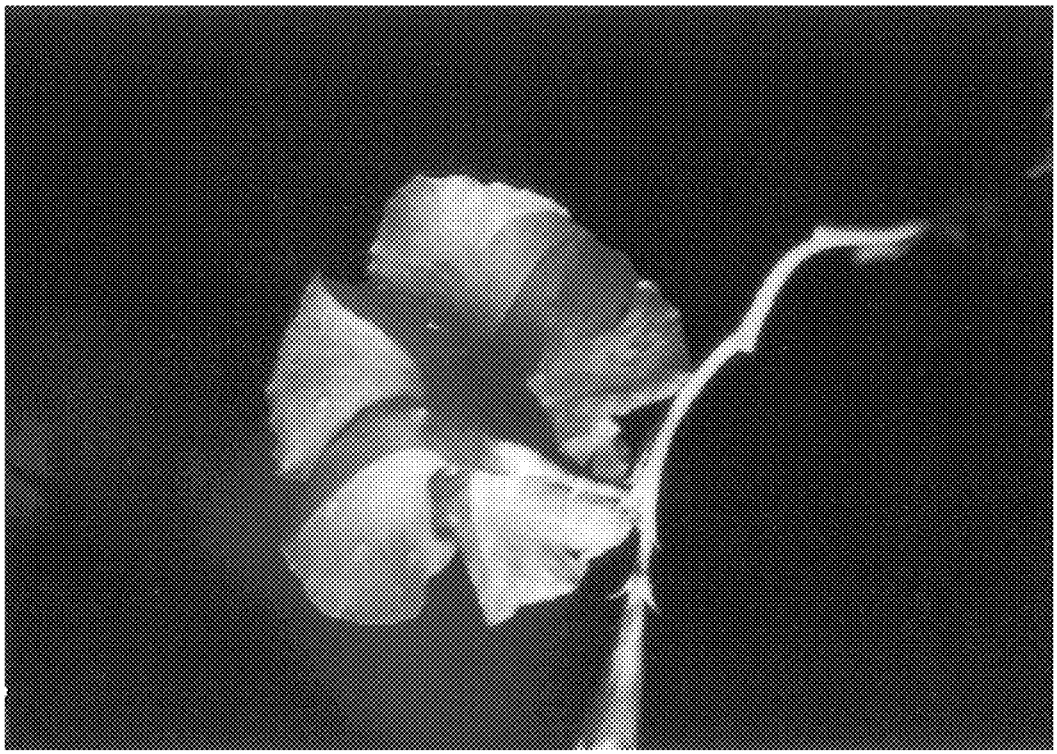
FIG. 2 is an posterior view of the double flower bloom of 'Rita Marie Green' showing the outer five-parted corolla attached to the stem.
Figure 3:
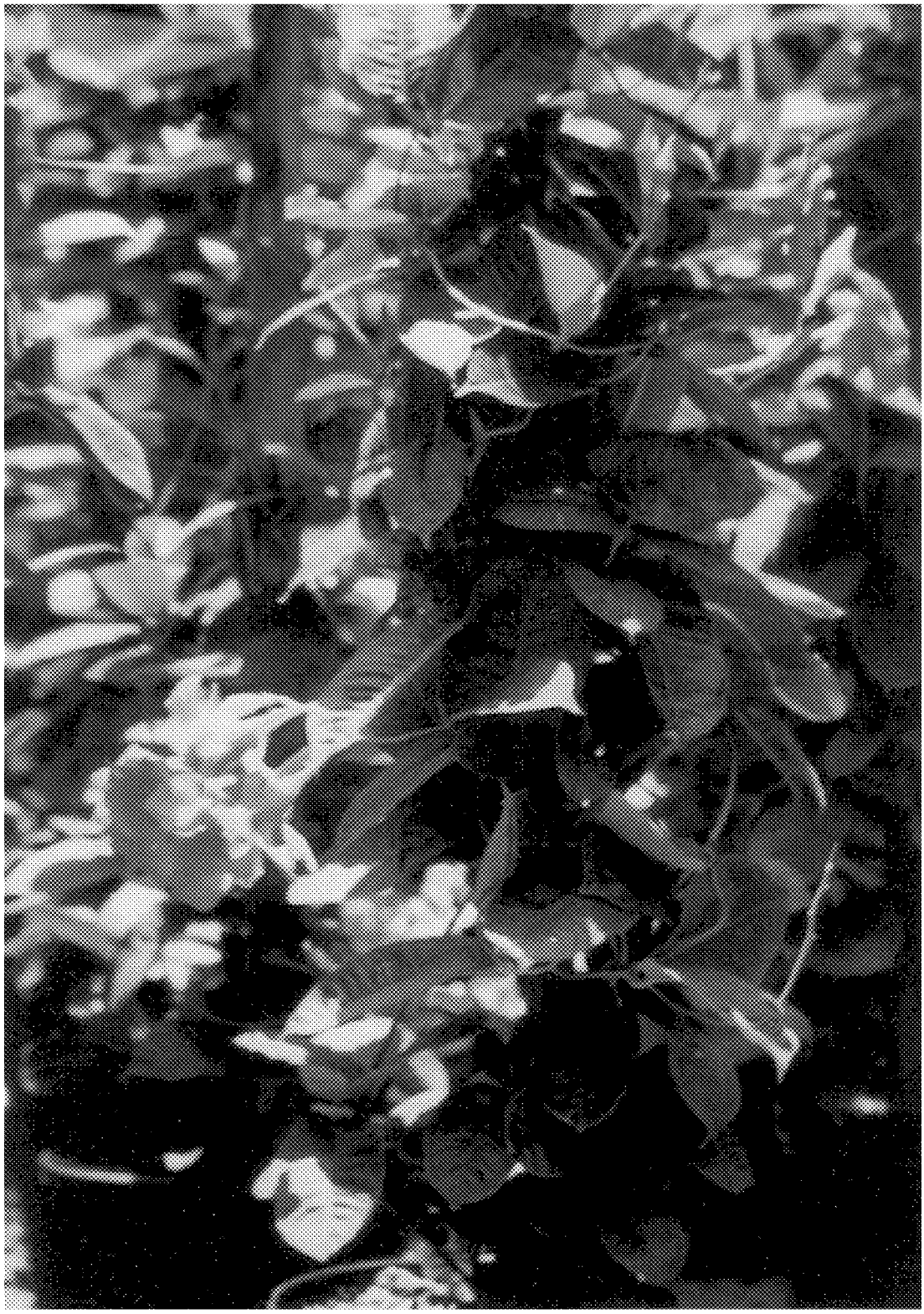
FIG. 3 is a view of the foliage of 'Rita Marie Green' showing its elliptic green leaves.

The following is a detailed description of the invention based on plants grown at the inventors' nursery in Haines City, Fla., and at a nursery in Azusa, Calif. All four of the double flower forms disclosed herein were obtained by growing plants of 'Rita Marie Green' in the same environmental conditions. Color descriptions are according to The Royal Horticultural Society Colour Chart. Other terminology is used herein in accordance with ordinary dictionary significance or as commonly used by those of ordinary skill in the relevant art, unless otherwise noted.

THE PLANT

Foliage:

*Type.*—Evergreen.

*Shape.*—Elliptic (linear to oblong). Apex: Long to short acuminate tip. Base: Cordate.

*Length.*—Variable from about 9.5 cm to 15 cm.

*Width.*—Variable from about 4.6 cm to 8.2 cm.

*Color.*—Upper foliage: Green group R.H.S. 139A to green group R.H.S. 137A. Lower foliage: Yellow-green group R.H.S. 146B. Arrangement on stem: Opposite. Margins: Entire. Habit: The 'Rita Marie Green' variety has a vigorous twining habit and is an ideal semi-tropical creeper. A mature plant of the variety 'Rita Marie Green' has twining stems 15 to 20 feet long and produces leaves that are large and glossy. Disease Resistance: The 'Rita Marie Green' variety is not known to be unusually tolerant to any pathogens. Frost Tolerance: The 'Rita Marie Green' variety is tolerant to temperatures as low as approximately 30° F. Fragrance: Flowers of the 'Rita Marie Green' variety have a slight sweet fragrance.

Flowers:

*Form* 1.—Arrangement: Axillary racemes. Color: Upper surface of petals. Corolla and petaloids: Red-purple group R.H.S. 58B and 58C. Petaloids (within throat): Slight striations of white group R.H.S. 155A and 155B and yellow group R.H.S. 2 within 1 cm of base of inner throat. Corolla (within throat): Yellow group R.H.S. 2 within 2 cm of base of inner throat. Underside of petals: Red-purple group R.H.S. 58B and 58C, mixed with red-purple R.H.S. group 62A, 62B, 62C, and 62D and white group R.H.S. 155D. Reproductive structures: Style: Generally present, about 8 mm to 11 mm in length. Stamens: Absent, developed into showy petals. Structure: Overall, funnel shaped. Likely reproductive structures are sterile due to "double" flowers with typical five-numbered stamens converted to petaloids. Outer five parted funnel-shaped corolla limbs. Inner five parted petaloids. Petaloids within the corolla to form a double flower. Corolla: Width: about 10.5 cm to 11.0 cm. Length of throat from calyx to corolla limb attachment: about 4.4 cm to 4.9 cm. Length of corolla from calyx to top of corolla: about 5.5 cm to 6.5 cm. Individual corolla limbs: 4.0 cm to 5.0 cm long, 3.5 cm to 5.5 cm wide. Asymmetrical in shape, ending in a short, abrupt tip. Petaloids (converted stamens): Individual petaloid length: about 4.0 cm to 4.5 cm. Individual petaloid width: about 3.5 cm to 5.0 cm. Petaloid attachment: about 1.5 cm above top of calyx. Petaloid fusion: Fused about 1.5 cm to 2.0 cm at base. Shape: Symmetrical short, abrupt tip. Petaloids are flattened and opened, resembling outer corolla. Length approximately equal to outer corolla, exhibiting a fully double appearance. Petaloids overlay corolla limbs exposing yellow inner base of tube.

*Form* 2.—Overall Structure: Funnel shaped. Outer five parted corolla limbs. Inner five parted petaloids. Petaloids have defined difference; shorter than corolla and remain in a cluster within center of corolla, not opening flat as in Form 1. Tight cluster habit of petaloids generally prohibits view of inner throat. Cluster of flower within flower. Corolla: Width: about 9.0 cm to 10.5 cm. Length of throat from calyx to corolla limb attachment: about 4.3 cm to 4.8 cm. Length of corolla from calyx to top of corolla: about 6.0 cm to 7.0 cm. Individual corolla limbs: about 4.0 cm to 5.0 cm long, 3.6 cm to 4.6 cm wide. Asymmetrical in shape, ending in an abrupt tip. Petaloids (converted stamens): Individual petaloid length: about 3.5 cm to 5.0 cm. Individual petaloid width: about 4.0 cm to 5.2 cm. Petaloid attachment: about 1.5 cm above top of calyx. Petaloid fusion: Fused, sometimes separated 2.0 cm at base. Shape: Somewhat symmetrical, undulate. Petaloids have defined distance, shorter than corolla and remaining in a cluster within outer corolla, not opening flat as in Form 1. Tight cluster habit of petaloids generally prohibits view of inner throat. Cluster of flower within flower.

*Form* 3.—Rarely observed, inner five petaloids folded to provide a rose flower-like appearance. Overall Structure: Outer five parted corolla limbs, inner five parted petaloids. Width of corolla: 9–10.5 cm. Length of corolla throat from calyx to corolla limb attachment: 4.3–4.8 cm. Length of corolla from calyx to top of corolla: 6–7 cm. Outer corolla limbs: 4.5 cm. long. Inner petaloids: 4 cm long. Reproductive Structures: Style: Absent. Stamens: Absent. Shape: Inner petaloids flattened and opened, resembling outer corolla. Similar to Form #1. Color: Corolla and petaloids: Red-purple group 58B and 58C, and red-purple group 62B, 62C and 62D. Petaloids within throat exhibit white blotches and streaks of white group 155A and 155B, and yellow group 2 within one centimeter of inner throat. Corolla within throat: Yellow group 2 within 1.5 cm of base of inner throat.

*Form* 4.—Rarely observed, inner five petaloids assume a windmill-like appearance. Overall structure: Outer five parted corolla limbs, inner five parted petaloids. Width of corolla: 9 cm. Length of corolla from calyx to top of corolla: 6 cm. Outer corolla limbs: 4 cm. Inner petaloids: 3 cm. Reproductive structures: Style: Absent. Stamens: Absent. Color: Corolla and petaloids: Red-purple group 58B and 58C, and red-purple group 62A, 62B, 62C and 62D, interspersed with mottled white blotches on petaloids green-yellow at base 3 mm by 2 mm.

The reason for the varied appearance of the double flowers has yet to be determined. However, the red to red-purple double flower characteristics are established and transmitted through succeeding asexual propagations.

Asexual reproduction of 'Rita Marie Green' has been performed from cuttings. Other conventional methods for propagation of Mandevilla varieties may also be used.

What is claimed is:

1. A new and distinct variety of Mandevilla plant having red to red-purple double flowers substantially as shown and described herein.

* * * * *

UNITED STATES PATENT AND TRADEMARK OFFICE

CERTIFICATE OF CORRECTION

PATENT NO. : PP 11,787 P2
DATED : February 27, 2001
INVENTOR(S) : Green et al.

It is certified that error appears in the above-identified patent and that said Letters Patent is hereby corrected as shown below:

Column 1,
Line 13, "Pont', which" should read -- Pont' (unpatented), which --.
Line 18, "The parent plant" should read -- The original plant --.
Line 22, "a mutation" should read -- a limb mutation --.
Line 24, "parent" should read -- original --.

Column 2,
Line 9, "the variety" should read -- the proprietary variety --.

Column 3,
Line 44, "R.H.S. 2" should read -- R.H.S. 2A --.
Line 46, "R.H.S. 2" should read -- R.H.S. 2A --.
Line 52, "petals" should read -- petaloids --.

Column 4,
Line 43, "group 2" should read -- group R.H.S. 2A --.
Line 44, "Yellow group 2" should read -- Yellow group R.H.S. 2A --.

Signed and Sealed this

Third Day of December, 2002

JAMES E. ROGAN
*Director of the United States Patent and Trademark Office*